US00PP22701P3

(12) United States Plant Patent
Bridgen

(10) Patent No.: US PP22,701 P3
(45) Date of Patent: May 1, 2012

(54) ***ALSTROEMERIA* PLANT NAMED 'TANGERINE TANGO'**

(50) Latin Name: ***Alstroemeria* hybrid L.**
Varietal Denomination: Tangerine Tango

(75) Inventor: Mark P. Bridgen, Southhold, NY (US)

(73) Assignee: Cornell University Cornell Ctr. for Technology, Enterprise & Commercialization, Ithaca, NY (US)

( * ) Notice: Subject to any disclaimer, the term of this patent is extended or adjusted under 35 U.S.C. 154(b) by 0 days.

(21) Appl. No.: 12/800,202

(22) Filed: May 11, 2010

(65) Prior Publication Data

US 2010/0293686 P1 Nov. 18, 2010

Related U.S. Application Data

(60) Provisional application No. 61/216,010, filed on May 12, 2009.

(51) Int. Cl.
*A01H 5/00* (2006.01)

(52) U.S. Cl. ..... Plt./309

(58) Field of Classification Search ..... Plt./309
See application file for complete search history.

*Primary Examiner* — June Hwu

(74) *Attorney, Agent, or Firm* — Jondle & Associates, P.C.

(57) ABSTRACT

An *Alstroemeria* variety particularly distinguished by bright orange inflorescences with yellow highlights, good longevity as a cut flower, continuous flowering from summer through fall, and winter-hardy from USDA zone 5 or warmer, is disclosed.

2 Drawing Sheets

Genus and species: *Alstroemeria* hybrid L.

Variety denomination: 'Tangerine Tango'.

ACKNOWLEDGEMENT OF FEDERAL RESEARCH SUPPORT

This invention was made, at least in part, with government support under Hatch Funding from the U.S. Department of Agriculture, Project Number NYC-145302, in cooperation with Cornell University's State Agricultural Experiment Stations. Accordingly, the United States government has certain rights in this invention.

CROSS REFERENCE TO RELATED APPLICATIONS

This application claims priority under 35 U.S.C. §119 from U.S. Provisional Application No. 61/216,010, filed on May 12, 2009, which is incorporated herein in its entirety by reference.

BACKGROUND OF THE NEW PLANT

The present invention comprises a new and distinct variety of *Alstroemeria,* botanically known as *Alstroemeria* hybrid L., and hereinafter referred to by the variety name 'Tangerine Tango'. 'Tangerine Tango' originated from a hybridization made in April 2002 in Riverhead, N.Y. The female parent was an un-named individual plant of *Alstroemeria aurea* plant (unpatented), while the male parent was a proprietary *Alstroemeria* plant '00-0203' (unpatented).

'Tangerine Tango' was selected for its distinctive bright orange inflorescences with yellow highlights, continuous flowering and strong, upright flower stems.

'Tangerine Tango' has been asexually propagated repeatedly by in vitro micropropagation and whole-plant division of rhizomes in Riverhead, N.Y. since Fall 2002 for approximately ten generations and has been found to retain its distinctive characteristics through successive asexual propagations.

SUMMARY OF THE INVENTION

The following are the most outstanding and distinguishing characteristics of this new variety when grown under normal commercial practices in a greenhouse or outdoor field in Riverhead, N.Y.

1. Bright orange inflorescences with yellow highlights;
2. Has good longevity as a cut flower;
3. Continuous flowering from summer through fall; and
4. Winter-hardy from USDA zone 5 or warmer.

DESCRIPTION OF THE PHOTOGRAPHS

This new *Alstroemeria* plant is illustrated by the accompanying photographs which show blooms and foliage of the plant. The colors shown are as true as can be reasonably obtained by conventional photographic procedures. The plants in the photographs are approximately one year old.

DESCRIPTION OF THE NEW VARIETY

Figure 1:
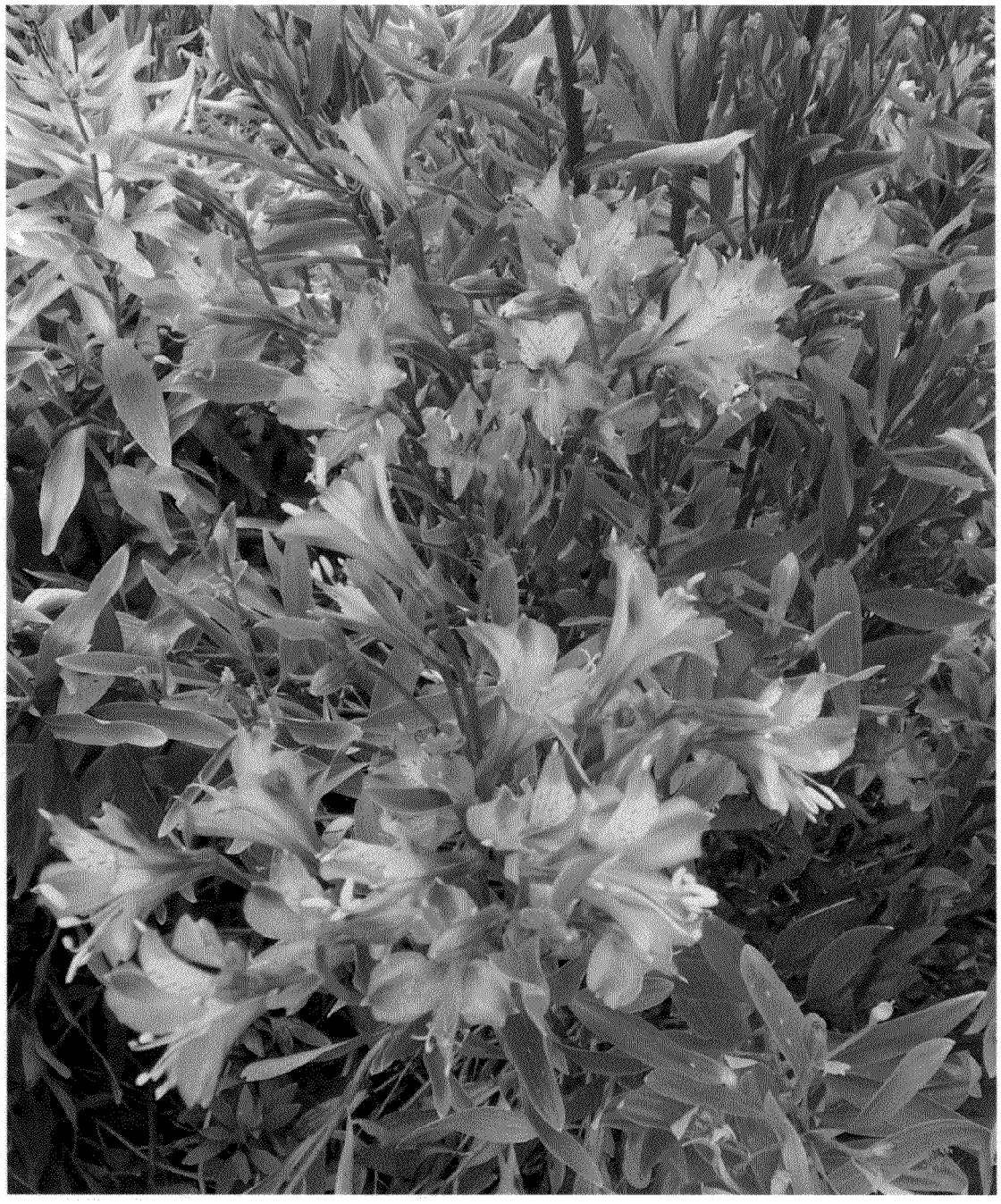
FIG. 1 shows the overall plant habit, including mature inflorescences, flower buds, and leaves.
Figure 2:
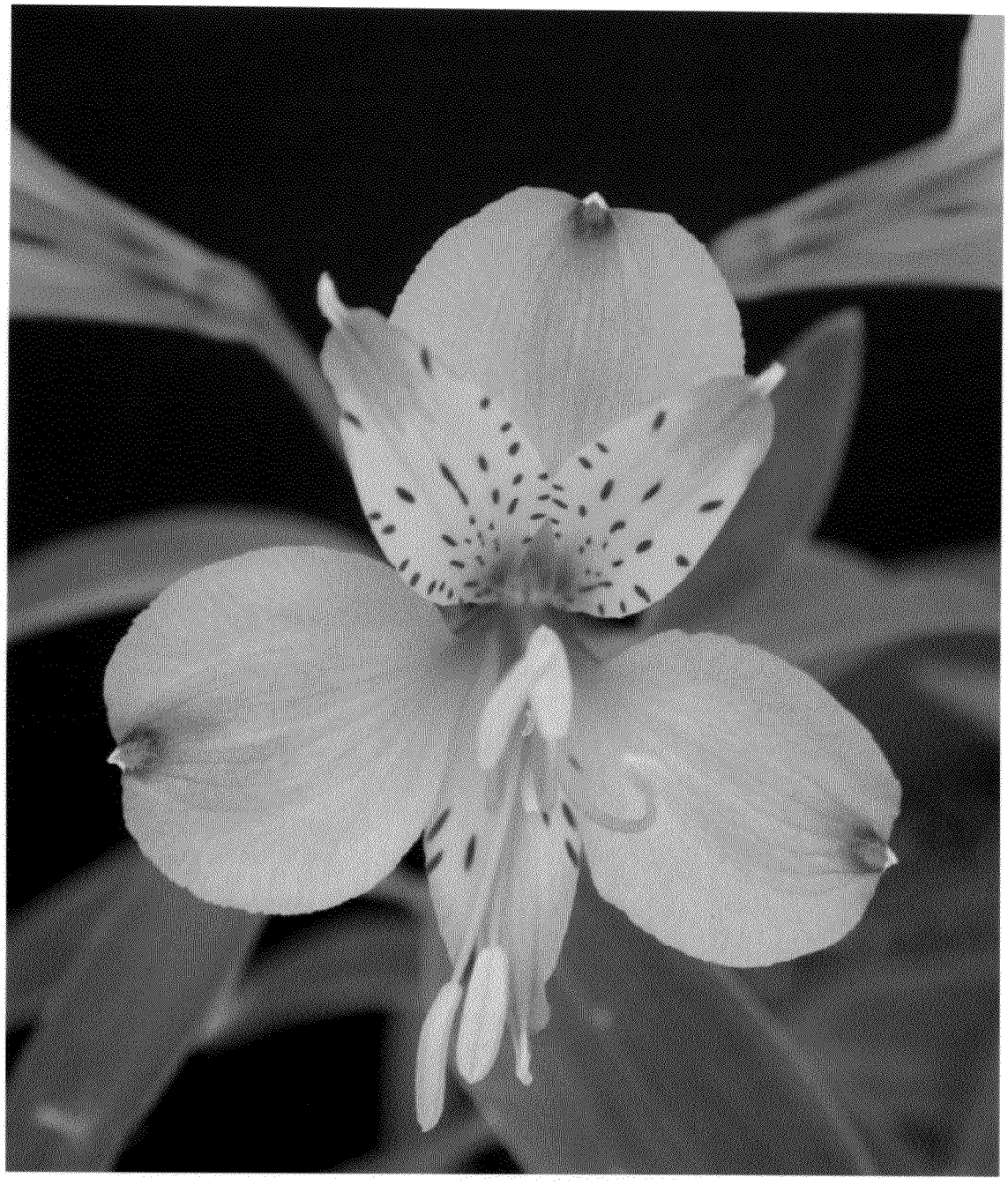
FIG. 2 shows a close-up of the mature inflorescence.

The following detailed descriptions set forth the distinctive characteristics of 'Tangerine Tango'. The data which define these characteristics were collected from asexual reproductions carried out in Riverhead, N.Y. from approximately one-year-old plants. The data were collected in the summer and fall on plants grown outdoors in full sun. Color references are primarily to The R.H.S. Colour Chart of The Royal Horticultural Society of London (R.H.S.), 2001.

DETAILED BOTANICAL DESCRIPTION

Classification:

*Botanical.*—*Alstroemeria* hybrid L.

*Common name.*—*Alstroemeria,* Lily-of-the-Incas, Inca Lily, Peruvian Lily.

*Denomination.*—'Tangerine Tango'.

Parentage:

*Female parent.*—An un-named individual plant of *Alstroemeria aurea* plant (unpatented).

*Male parent.*—The proprietary *Alstroemeria* plant '00-0203' (unpatented).

Plant:

*Form.*—Herbaceous plant arising from an underground rhizome.

*Habit.*—Upright and vigorous.

*Plant height.*—75.0 cm to 80.0 cm.

*Plant width (spread).*—90.0 cm to 100.0 cm.

*Flowering habit.*—Continuous flowering from the beginning of summer until the first hard freeze in fall.

*Time to produce a finished flowering plant.*—If a clump is divided in the spring or early summer, it will resume flowering within a month.

Flowering stems:

*Color.*—RHS 137A or RHS 137C (Green).

*General description.*—Long, strong, and upright growing floral stems.

*Stem strength.*—Strong.

*Surface texture.*—Glabrous and smooth.

*Length.*—62.5 cm to 90.0 cm.

*Diameter.*—0.5 cm to 1.0 cm.

*Internode length.*—Not applicable.

Leaves:

*Arrangement.*—Simple, linear, resupinate leaves with parallel venation that is arranged alternately.

*Shape.*—Elongated and elliptical with extended bases.

*Apex.*—Broadly acuminate.

*Base.*—Extended.

*Margin.*—Entire.

*Color, mature leaf (both surfaces).*—RHS 137A or RHS 137C (Green).

*Length.*—10.0 cm.

*Width.*—2.2 cm.

*Texture.*—Glabrous. Upper surface: Glabrous and smooth. Lower surface: Glabrous but not as smooth.

*Venation pattern.*—Parallel.

*Petiole.*—Absent (sessile leaves).

Inflorescence:

*Type.*—A terminal bracted-umbel composed of cymes.

*Flowering season.*—Early summer through early fall.

*Lastingness of inflorescences on the plant.*—15 to 21 days.

*Flower width.*—Approximately 4.5 cm to 5.0 cm at the open end.

*Flower depth.*—3.7 cm to 4.2 cm.

*Flower shape.*—Tubular.

*Fragrance.*—Absent.

*Quantity of individual flowers per plant.*—Everblooming; varies with size of plant; 30 to 50 every three months.

*Number of florets per umbel.*—Typical: 10. Range: 5 to 15.

*Peduncle.*—Length: 2.5 cm to 4.0 cm. Diameter: Approximately 0.4 cm to 0.6 cm. Surface texture: Glabrous and smooth. Color: RHS 137A (Green) or RHS 137C (Green).

*Umbel diameter.*—Approximately 10.0 cm to 15.0 cm.

*Lastingness of the blooms.*—12 to 14 days for a fresh cut flower in a vase.

Flower buds:

*Color.*—RHS 146C (Yellow-green) and RHS 139C (Green) to RHS 137C (Green) towards the tip; RHS 183A (Greyed-purple) at the base.

*Shape.*—Pear-shaped and becoming long and more pointed just before opening.

*Length.*—Approximately 2.5 cm to 2.8 cm before opening.

*Diameter.*—Approximately 0.9 cm to 1.0 cm before opening.

Tepals:

*Arrangement.*—Composed of two concentric circles of three tepals each: an outer circle of three (sepals) and an inner circle of three (petals).

*Shape.*—Tubular/spatulate to oblanceolate-spatulate.

*Apex.*—Emarginate to mucronate to apiculate.

*Length.*—3.7 cm to 4.2 cm.

*Width.*—Outer tepals (sepals): Approximately 1.5 cm to 2.0 cm at the widest point. Inner tepals (petals): Approximately 0.5 cm to 1.0 cm.

*Texture.*—Upper surface: Glabrous and smooth. Lower surface: Glabrous but not as smooth.

*Color of mature and immature plants when grown in full sun.*—Outer tepals, upper surface (sepals): Mostly RHS 169C (Greyed-orange) to RHS 28B (Orange) with RHS 23A (Yellow-orange) at the base. There are no flecks present and their apices are RHS 139C to 137C (Green). Inner tepals, upper surface (petals): The two top of the three are mostly RHS 14A (Yellow-orange) on the bottom 80%. Also present are short, narrow, flecks approximately 2 to 7 mm in length which are colored RHS 183A (Greyed-purple). The lower surfaces of both outer tepals and inner tepals are similar to the color description as the upper surface, outer tepals and inner tepals except no flecks present.

Reproductive organs:

*Pistals.*—Quantity: 1. Style length: 2.5 cm to 4.0 cm. Style color: RHS 28B (Orange).

*Stamens.*—Quantity: 6. Filament length: Approximately 2.5 cm to 4.0 cm. Filament color: RHS 28B (Orange). Anther length: 3.0 mm. Anther width: 2.0 mm. Anther color: RHS 22A (Yellow-orange). Pollen: Flowers are sterile; no viable pollen is produced.

Seeds: No seeds have been observed.

Disease and insect resistance: Thrips are less likely to attack. Disease resistance is typical of the species.

COMPARISON WITH PARENTAL AND COMMERCIAL VARIETIES

'Tangerine Tango' differs from the female parent, an unnamed individual plant of *Alstroemeria aurea* (unpatented), in that 'Tangerine Tango' has larger inflorescences and shorter peduncles than the female parent. Additionally, 'Tangerine Tango' is everblooming and blooms for a longer period of time than the female parent.

'Tangerine Tango' differs from the male parent, the proprietary *Alstroemeria* plant '00-0203' (unpatented), in that 'Tangerine Tango' has larger inflorescences and a longer blooming time than '00-0203'.

'Tangerine Tango' differs from the commercial *Alstroemeria* variety 'Mauve Majesty' (U.S. Plant Pat. No. 18,183), by having orange inflorescences with yellow highlights, while 'Mauve Majesty' has pale-purple inflorescences.

I claim:

1. A new and distinct variety of *Alstroemeria* plant named 'Tangerine Tango' as described and shown herein.

* * * * *